United States Patent [19]

Houlihan et al.

[11] 3,959,269

[45] May 25, 1976

[54] 2-SUBSTITUTED-3-DISUBSTITUTED-4,5,6,7-SUBSTITUTED OR UNSUBSTITUTED PHTHALIMIDINES

[75] Inventors: William J. Houlihan, Baden, Austria; Jeffrey Nadelson, Lake Parsippany, N.J.

[73] Assignee: Sandoz, Inc., E. Hanover, N.J.

[22] Filed: July 12, 1974

[21] Appl. No.: 488,041

Related U.S. Application Data

[60] Division of Ser. No. 232,615, March 7, 1972, Pat. No. 3,849,438, which is a continuation-in-part of Ser. No. 126,272, March 19, 1971, abandoned.

[52] U.S. Cl. ............................................. 260/343.3 R
[51] Int. Cl.² ................................................ C07D 493/00
[58] Field of Search ............................... 260/343.3

[56] References Cited

UNITED STATES PATENTS 3,812,181   5/1974   Leimgruber .................. 260/520

*Primary Examiner*—James A. Patten
*Attorney, Agent, or Firm*—Gerald D. Sharkin; Robert S. Honor; Walter F. Jewell

[57] ABSTRACT

2-Substituted-3-disubstituted-4,5,6,7-substituted or unsubstituted phthalimidines, e.g., 3-t-butyl-5-chloro-3-hydroxy-2-methylphthalimidine prepared by treating a substituted or unsubstituted N-substituted-2-lithiobenzamidelithium salts with a substituted acetylhalide. The compounds are useful as minor tranquilizers/sedative hypnotics.

1 Claim, No Drawings

2-SUBSTITUTED-3-DISUBSTITUTED-4,5,6,7-SUBSTITUTED OR UNSUBSTITUTED PHTHALIMIDINES

This is a division of application Ser. No. 232,615 filed Mar. 7, 1972, now U.S. Pat. No. 3,849,438, which is a continuation-in-part of application Ser. No. 126,272, filed Mar. 19, 1971, now abandoned.

This invention relates to 2,3-substituted-4,5,6,7-substituted or unsubstituted phthalimidines. More particularly, it relates to 2-substituted-3-disubstituted-4,5,6,7-substituted or unsubstituted phthalimidines, intermediates thereof and to processes for their preparation.

The compounds of this invention may be represented by the following structural formula:

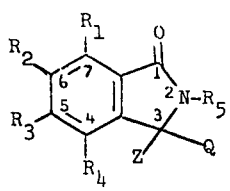

(I)

where
- $R_1$ is hydrogen, lower alkoxy having 1 to 4 carbon atoms, e.g., methoxy, ethoxy, propoxy, isopropoxy, butoxy or isobutoxy, halo having an atomic weight of 19 to 36, or trifluoromethyl;
- $R_2$ is hydrogen, lower alkyl having 1 to 4 carbon atoms, e.g., methyl, ethyl, propyl, isopropyl, butyl or isobutyl, lower alkoxy as defined above, halo as defined above, trifluoromethyl, nitro or amino;
- $R_3$ is hydrogen, lower alkyl as defined above, lower alkoxy as defined above, halo as defined above, trifluoromethyl, nitro, amino, dialkylamino wherein alkyl is as defined above or phenyl;
- $R_4$ is hydrogen, lower alkyl as defined above, lower alkoxy as defined above, or trifluoromethyl;
- $R_5$ is hydrogen, lower alkyl as defined above, phenyl, allyl, benzyl, hydroxyethyl, carbamoyloxy, or carbethoxymethyl; or
- $R_1$ and $R_2$, $R_2$ and $R_3$, or $R_3$ and $R_4$ together are methylenedioxy, Q is

where $R_6$ and $R_7$ are each independently methyl or ethyl; or
$R_6$ and $R_7$ together are $-(CH_2)_n-$
where $n$ is 4, 5 or 6;
$R_8$ is methyl, vinyl or allyl, or

where $R_9$ is lower alkyl having 1 to 4 carbon atoms, as defined above;
Z is hydroxy, amino, lower alkoxy as defined above, or

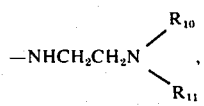

where $R_{10}$ and $R_{11}$ are independently lower alkyl as defined above,
provided that
1. no more than two of $R_1$, $R_2$, $R_3$ or $R_4$ are other than hydrogen;
2. when either or $R_1$ or $R_3$ is halo, the other of $R_1$ or $R_3$ is not halo;
3. only one of $R_1$ and $R_3$, or $R_2$ and $R_4$ is alkoxy at one time;
4. there are no two trifluoromethyl groups on adjacent carbon atoms;
5. only one of $R_2$ or $R_3$ is nitro or amino;
6. when Z is hydroxy and Q is t-butyl, then $R_1$, $R_2$, $R_3$, $R_4$ and $R_5$ are not hydrogen.

The compounds of formula (I) where Z is hydroxy ($Z°$) (Ia) may be prepared by the following reaction scheme A:

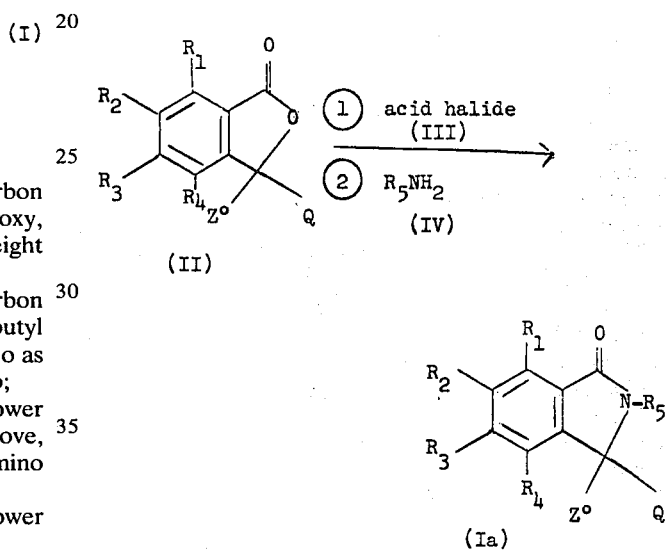

wherein $R_1$, $R_2$, $R_3$, $R_4$, $R_5$, Q, $Z°$ and the provisos have the above stated significance.

The compounds of (Ia) may be prepared by treating a compound of formula (II) with an acid halide (III) such as thionyl chloride, phosphorous pentachloride, thionyl bromide and the like in an inert solvent such as benzene, ether, methylene dichloride and the like and then treating the resulting adduct with a compound of formula (IV). The reaction may be carried out at a temperature of from 0°C to the reflux temperature of the solvent, preferably 25°C to the reflux temperature, for about 1 to 3 hours, preferably about 2 hours. Neither the solvents nor the temperature used are critical.

The compounds of the formula (Ia) may also be illustrated by their tautomeric equivalent such as represented by the following structural formula:

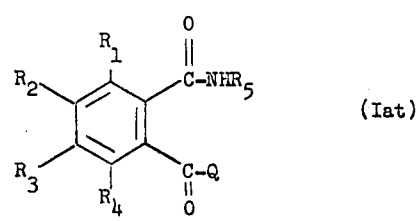

wherein $R_1$, $R_2$, $R_3$, $R_4$, $R_5$, Q and the provisos have the above-stated significance.

In order to simplify this description, however, formula (Ia) only will be used. It should be nevertheless understood that the compounds of formula (Iat) may be represented as well as the compounds of formula (Ia) and the two tautomeric forms are within the concept of the present invention.

The compounds of formula (I) where Z is amino (Z') and $R_1$, $R_2$, $R_3$, $R_4$, $R_5$, Q and the provisos are as stated above (Ib), may be prepared by the following reaction scheme B, wherein a compound of formula (Ia) in the first step is treated with an acid halide (III). Inert aromatic solvents such as benzene, toluene, xylene and the like may be used. Reaction temperatures may be from about 50° to 175°C preferably 75° to 150°C, and if a solvent is used from about 50° to the reflux temperature of the solvent, preferably at the solvent reflux temperature. Reaction times are from about 1 to 10 hours preferably 2 to 5 hours. The resulting adduct is treated in the second step with saturated ammonia in an inert solvent such as benzene, tetrahydrofuran, methylene chloride and the like at from about room temperature to the reflux temperature of the solvent, preferably at room temperature for about 1 to 24 hours. Neither the solvents nor the temperatures used are critical.

The compounds of formula (I) where Z is lower alkoxy having 1 to 4 carbon atoms (Z'') and $R_1$, $R_2$, $R_3$, $R_4$, $R_5$ and Q are as defined above (Ic) may be prepared by the following reaction scheme C, wherein a compound of formula (Ia) in the first step is treated with an acid halide (III). Inert aromatic solvents such as benzene, toluene, xylene and the like may be used. Reaction temperatures may be from about 50° to the reflux temperature of the solvent, preferably at the solvent reflux temperature. Reaction times are from about 1 to 10 hours preferably 2 to 5 hours. The resulting adduct is treated in the second step with a lower alkanol (V) having 1 to 4 carbon atoms such as methanol, propanol, isobutanol and the like at from about room temperature to reflux temperature of the alkanol, preferably at room temperature for about 1–24 hours. Neither the solvents nor the temperatures used are critical.

The compounds of formula (I) where Z is

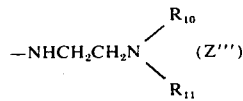

wherein $R_{10}$ and $R_{11}$ are as defined above, and $R_1$, $R_2$, $R_3$, $R_4$, $R_5$ and Q are as defined above (Id) may be prepared by the following reaction scheme D, wherein a compound of formula (Ia) in the first step is treated with an acid halide (III) using the solvents and under the reaction conditions described in reaction scheme C. The resulting adduct is treated in the second step with a substituted amine of the formula:

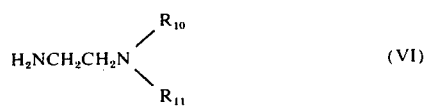

wherein $R_{10}$ and $R_{11}$ have the above-stated significance. When the amine of formula (VI) is not liquid, an inert solvent such as benzene, methylene chloride and the like must be used. Reaction temperatures may be from about 15° to 150°C, of if a solvent is used from 20°C to the reflux temperature of the solvent. The convenient temperature is about 20° to 25°C. Neither the solvents nor the temperatures used are critical.

The compounds of formula (Ia) where $R_5$ is lower alkyl, or phenyl ($R_5^o$) (Ia$_1$), may also be prepared by the following reaction scheme $A_1$:

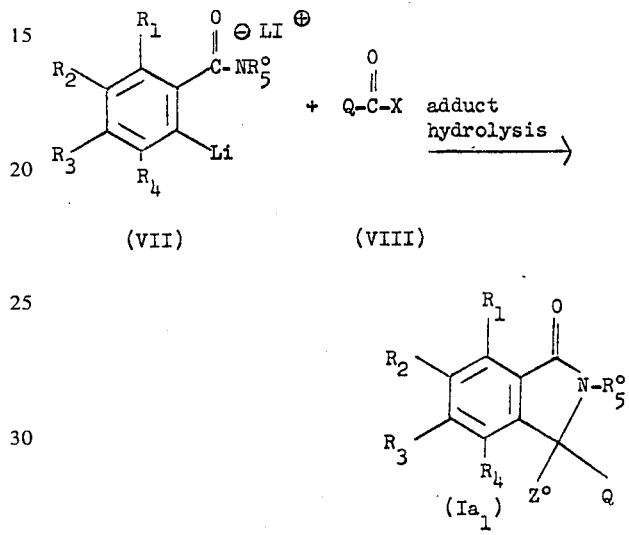

wherein $R_1$, $R_2$, $R_3$, $R_4$, $R_5^o$, Q and $Z^o$ and the provisos have the above-stated significance, X is halo having an atomic weight of 35 to 80, or $-OR_{12}$ where $R_{12}$ is methyl or ethyl.

The compounds of formula (Ia$_1$) may be prepared by treating a compound of formula (VII) with a compound of formula (VIII) in an inert solvent such as diethyl ether, tetrahydrofuran, hexane, heptane or the like, in the presence of an inert gas, e.g. nitrogen, helium or argon and then subjecting the reaction mixture to conventional hydrolysis, preferably with aqueous ammonium chloride. The reaction may be carried out at a temperature of from −60° to −40°C., preferably −55° to −45°C., for about 1 to 3 hours preferably about 2 hours. Neither the solvents nor the temperatures used are critical.

The compound of formula (Ib) where $R_5^o$ is as defined above (Ib$_1$) may be prepared by the following reaction scheme $B_1$, wherein a compound of formula (VII) is treated with a compound of formula Q—C ≡ N (IX) where Q is as stated above, in an inert solvent, in the presence of an inert gas as indicated in reaction scheme $A_1$, and subjecting the reaction mixture to conventional hydrolysis, preferably with aqueous ammonium chloride. The reaction may be carried out at a temperature of from −5° to the reflux temperature of the solvent, preferably 50°C. to the solvent reflux temperature for about 1 to 8 hours, preferably about 6 hours. Neither the solvents nor the temperatures used are critical.

The compounds of formula (Ic) where $R_5$ is lower alkyl or phenyl (Ic$_1$) may also be prepared by the following reaction scheme $C_1$, wherein a compound (Ia$_1$) is treated in the same manner as compounds (Ia) in reaction scheme C.

The compounds of formula Id where $R_5$ is lower alkyl or phenyl ($Id_1$) may also be prepared by the following reaction scheme $D_1$, wherein a compound of formula ($Ia_1$) is treated in the same manner as compounds (Ia) in reaction scheme D.

The compounds of formula ($Ia_1$) wherein Q is butyl, $R_1$ and $R_4$ are hydrogen, lower alkoxy as defined above or trifluoromethyl, ($R_1°$) and ($R_4°$), $R_2$ and $R_3$ are hydrogen, lower alkyl as defined above, lower alkoxy as defined above, or halo as defined above, ($R_2°$) ($R_3°$) may be prepared by the following reaction scheme E.

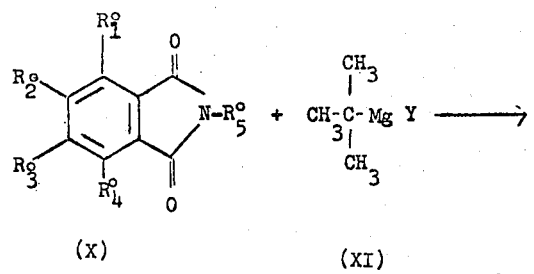

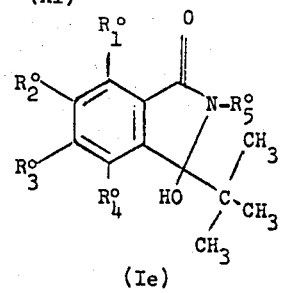

wherein $R_1°$, $R_2°$, $R_3°$ and $R_4°$ are as defined above, $R_5°$ is as previously defined, and Y is halo having an atomic weight of 35 to 80.

The compounds of formula (Ie) may be prepared by treating a compound of formula (X) with t-butyl magnesium halide of formula (XI), in an inert solvent such as ether, tetrahydrofuran and the like in an inert atmosphere e.g. nitrogen, at a temperature of from about 25°C to the reflux temperature of the solvent, preferably at the solvent reflux temperature, for about 3 to 24 hours, preferably about 16 to 20 hours. Neither the solvents nor the temperatures used are critical. Reaction scheme E is preferred for preparing compounds of formula ($Ie_1$) wherein $R_1$ and $R_4$ are hydrogen and $R_2$ and $R_3$ are other than hydrogen.

The compounds of formula (I) where $R_1$ and $R_4$ are hydrogen, $R_5$ is methyl, Z is hydroxy, Q is tert-butyl and $R_2$ or $R_3$ is nitro (If) may be prepared by the following reaction scheme F:

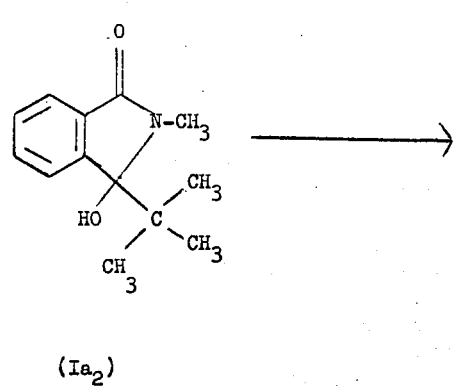

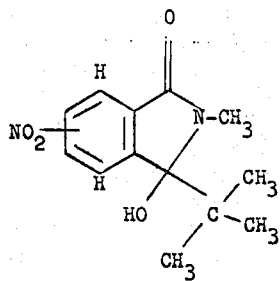

The compounds of formula (If) may be prepared by treating 3-t-butyl-3-hydroxy-2-methylphthalimidine ($Ia_2$) with alkali metal nitrate e.g. potassium nitrate in concentrated mineral acid e.g. sulfuric acid at a temperature of from about −20° to about 50°C preferably from about 0°C to 25°C for about 24 hours. The temperatures used are not critical. Reaction scheme F is preferred for preparing the compounds of formula (If).

The compounds of formula (II) may be prepared by the following reaction scheme G wherein a compound of formula ($Ia_1$) wherein $R_5°$ is methyl or phenyl ($Ia_3$) is treated with a strong base such as sodium hydroxide or potassium hydroxide in aqueous monohydric alkanol or dihydric alkanol such as methanol, ethanol, propanol, isopropanol, butanol, isobutanol, ethylene glycol and the like at a temperature of from 50°C to the reflux temperature of the solvent, preferably at the solvent reflux temperature, for about 12 to 72 hours, preferably 18 to 40 hours, and subsequently acidifying with concentrated mineral acid such as sulfuric acid, hydrochloric acid and the like.

The compounds of the formula (VII) may be prepared by the following reaction scheme H:

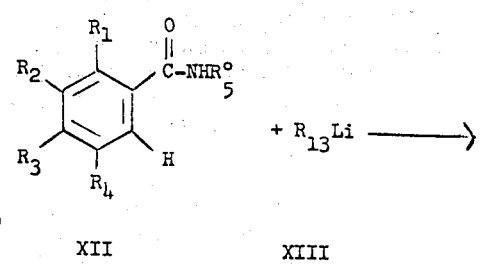

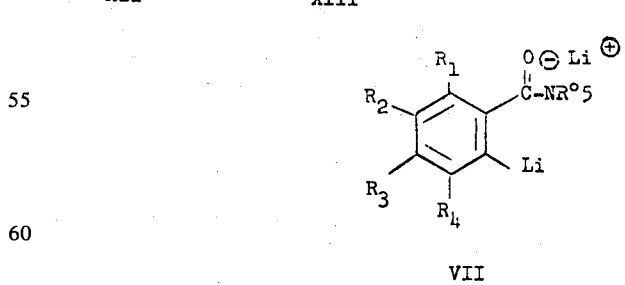

wherein $R_1$, $R_2$, $R_3$, $R_4$, $R_5$ and the provisos have the above stated significance, and $R_{13}$ is lower alkyl as defined above.

The compounds of formula (VII) are prepared by treating a compound of formula (XII) with an organo lithium compound of formula (XIII) in an inert solvent, in the presence of an inert gas as indicated in reaction scheme A₁. The reaction may be carried out at a temperature of from about −70° to 20°C.

The compounds of formulas (Ia), (Ib), (Ic), (Id), (Ia₁), (Ib₁), (Ic₁), (Id₁), (Ie₁), (If) and (II) may be recovered using conventional recovery techniques such as crystallization.

Certain of the compounds of formulas (X), (XI), (XII) and (XIII) are known and may be prepared according to methods disclosed in the literature. The compounds of formulas (X), (XI), (XII) and (XIII) not specifically disclosed are prepared according to analogous methods from known materials.

The compounds of formula (Ia) may be prepared in alkali metal salt form such as the sodium salt, potassium salt, lithium salt and the like by treating a compound of formula (Ia) with a base such as sodium hydroxide, potassium hydroxide or lithium hydroxide. When it is desired to convert such salts to the corresponding hydroxy compound, conventional techniques may be utilized.

The compounds of formulas (Ib) or (Id) may be prepared in acid addition salt form, such as the hydrochloride, by conventional methods, such as suspending the compound of alcohol or water and treating with the appropriate acid. When it is desired to convert such salts to the corresponding free bases, conventional techniques may be utilized, e.g., dissolution of the salt in water and precipitation using a base such as sodium hydroxide.

It will be understood that certain of the compounds of formula (I) can exist in racemic form or in the form of optically active isomers. The separation and recovery of the respective isomers may be readily accomplished employing conventional techniques and such isomers are included within the scope of the invention.

The compounds of formula (I) are useful because they possess pharmacological activity in animals. In particular, the compounds are useful as minor tranquilizers-sedative hypnotics, as indicated in the mouse given typically 25–200 mg/kg of body weight of the active compounds and tested using the 30-word adjective test basically as described by Irwin, S. (Gordon Research Conference, Medicinal Chemistry, 1959) and Chen (Symposium on Sedative and Hypnotic Drugs, Williams and Wilkins, 1954), the chemically induced seizures test basically as described by Orloff, et al., (Proc. Sol. Exp. Biol., 70: 254, 1949), the hexobarbital reinduction test, wherein immediately after the animals recover their righting reflex which was lost upon the administration of hexobarbital, "reinduction" is stated to occure if the animals once again lose their righting reflex, basically as described by Winter et al. J. Pharmacol. Exp. Therap. 94: 7–11, 1948, and the shock induced fighting mice test, basically as described by Tedeschi et al. J. Pharmacol. Exp. Therap. 125: 28–34, 1969.

For such usage, the compounds may be administered orally or parenterally as such or admixed with conventional pharmaceutical carriers.

The compounds of formula (Ia) may be administered in the form of their non-toxic alkali metal salts. Such salts possess the same order of activity as the free base. Representative of such salts are sodium, potassium or lithium salts, and the like.

The compounds of formulas (Ib) or (Id) may be similarly administered in the form of their non-toxic pharmaceutically acceptable acid addition salts. Such salts possess the same order of activity as the free base. Representative of such salts are the mineral acid salts, such as the hydrochloride, hydrobromide, sulfate, phosphate and the like and the organic acid salts, such as the succinate, benzoate, acetate, p-toluenesulfonate, benzenesulfonate, maleate, malate, tartrate, methanesulfonate, cyclohexylsulfamate and the like.

As noted above, the compounds of formula (I) exist as optical isomers. In some cases greater pharmacological activity or other beneficial attribute may be found for a particular isomer and in such instances administration of such isomer may be preferred.

The dosage of active ingredient employed for the tranquilizer-sedative hypnotic use may vary depending on the severity of the condition being treated. However, in general, satisfactory results are obtained when a compound of formula (I) is administered at a daily dosage of from about 1 milligram to about 300 milligrams per kilogram of animal body weight, preferably given in divided doses 2 to 4 times a day, or in sustained release form. For most larger mammals (e.g., primates) the total daily dosage is from about 60 to about 3000 milligrams. Dosage forms suitable for internal use comprise from about 15 to about 1500 milligrams of the active compound, in intimate admixture with a solid or liquid pharmaceutically acceptable carrier or diluent.

EXAMPLE 1

3-t-butyl-3-hydroxy-2-methylphthalimidine

To a flask equipped with a stirrer, dropping funnel, condenser and gas inlet tube maintained under a nitrogen atmosphere there was added at room temperature 15.2 g. (0.108 mole) of N-methylbenzamide in 150 ml. dry tetrahydrofuran. The reaction flask was immersed in an ice bath and cooled to an internal temperature of 5°C. Stirring was initiated and 152 ml. of 1.6M of n-butyllithium(0.240 mole) in hexane was added dropwise in ca.1 hour maintaining the temperature below 8°C. The resulting red dilithio salt, (Compound VII) was stirred at 5°C. for 1 hour longer and then cooled to an internal temperature of −50°C. To the cold solution, a solution of 12.9g. (0.108 mole) of trimethylacetylchloride (pivaloylchloride) in 75 ml. anhydrous tetrahydrofuran was added dropwise in ca. 45 minutes maintaining the temperature between −6° and −40°C. The resulting solution was stirred 2 hours at −50°C. and allowed to warm to 0°C. and the resulting adduct treated with 100 ml. saturated aqueous ammonium chloride maintaining the temperature below 10°C. The layers were separated and the tetrahydrofuran dried over anhydrous magnesium sulfate, filtered and evaporated in vacuo. The resulting oil was triturated with cold ether and filtered to give 3-t-butyl-3-hydroxy-2-methylphthalimidine m.p. 166.8°–167°C.

EXAMPLE 2

Following the procedure of Example 1 and in place of N-methylbenzamide and starting with,
a. N-methyl-4-methoxybenzamide,
b. 4-chloro-N-methylbenzamide,
c. 6-chloro-N-methylbenzamide,
d. N-phenylbenzamide,
e. 4-fluoro-N-methylbenzamide,
f. N-methyl-4-phenylbenzamide,
g. 4-dimethylamino-N-methylbenzamide,
h. 5-methoxy-N-methylbenzamide, i. N,4-dimethylbenzamide,
j. 4,5-dichloro-N-methylbenzamide,
k. 4-t-butyl-N-methylbenzamide,
l. 4-ethyl-N-methylbenzamide,
m. 6-chloro-N-methylbenzamide,
n. 3,4-dimethoxy-N-methylbenzamide,
o. N-methyl-4-nitrobenzamide,
p. N-methyl-4-aminobenzamide, or
q. N-methyl-4,5-methylenedioxybenzamide,
the following products are obtained
a. 3-t-butyl-3-hydroxy-5-methoxy-2-methylphthalimidine m.p. 165°–166.5°C.,
b. 3-t-butyl-5-chloro-3-hydroxy-2-methylphthalimidine m.p. 192°C.,
c. 3-t-butyl-7-chloro-3-hydroxy-2-methylphthalimidine m.p. 202.5°–203.5°C.,
d. 3-t-butyl-3-hydroxy-2-phenylphthalimidine m.p. 165°–165.5°C.,
e. 3-t-butyl-5-fluoro-3-hydroxy-2-methylphthalimidine m.p. 165°–167°C.,
f. 3-t-butyl-3-hydroxy-2-methyl-5-phenylphthalimidine m.p. 202°–203°C.,
g. 3-t-butyl-5-dimethylamino-3-hydroxy-2-methylphthalimidine m.p. 178°–183°C.,
h. 3-t-butyl-3-hydroxy-6-methoxy-2-methylphthalimidine m.p. 140.5°–141.5°C.,
i. 3-t-butyl-2,5-dimethyl-3-hydroxyphthalimidine m.p. 167°–169°C.,
j. 3-t-butyl-5,6-dichloro-3-hydroxy-2-methylphthalimidine m.p. 195.5°–196.5°C.,
k. 3,5-bis(t-butyl)-3-hydroxy-2-methylphthalimidine m.p. 182.5°–183.5°C.,
l. 3-t-butyl-5-ethyl-3-hydroxy-2-methylphthalimidine m.p. 136°–137°C.,
m. 3-t-butyl-5-chloro-2-ethyl-3-hydroxyphthalimidine m.p. 144°–145°C.,
n. 3-t-butyl-4,5-dimethoxy-3-hydroxy-2-methylphthalimidine m.p. 150°–151.5°C.,
o. 3-t-butyl-3-hydroxy-2-methyl-5-nitrophthalimidine,
p. 5-amino-3-t-butyl-3-hydroxy-2-methylphthalimidine, or
q. 3-t-butyl-3-hydroxy-2-methyl-5,6-methylenedioxyphthalimidine, respectively.

EXAMPLE 3

Following the procedure of Example 1 and in place of N-methylbenzamide and starting with,
a. N-methyl-6-methoxybenzamide,
b. N-methyl-3,6-bis(trifluoromethyl)benzamide,
c. N,3-dimethylbenzamide, or
d. N-methyl-3-methoxybenzamide,
the following products are obtained,
a. 3-t-butyl-3-hydroxy-7-methoxy-2-methylphthalimidine,
b. 3-t-butyl-3-hydroxy-2-methyl-4,7-bis(trifluoromethyl)phthalimidine,
c. 3-t-butyl-2,4-dimethyl-3-hydroxyphthalimidine, or
d. 3-t-butyl-3-hydroxy-4-methoxy-2-methylphthalimidine, respectively.

EXAMPLE 4

Following the procedure of Example 1 and in place of trimethylacetylchloride, and starting with,
a. 2,2-pentamethylenepropanoyl chloride, or
b. 2,2-hexamethylenepropanoyl chloride,
the following products are obtained,
a. 3-(1-[1,1-cyclopentamethylene]ethyl)-3-hydroxy-2-methylphthalimidine, m.p. 145.5°–146.5°C.,
d. 3-(1-[1,1-cyclohexamethylene]ethyl)-3-hydroxy-2-methylphthalimidine, m.p. 145.8°–146.5°C., respectively.

Following the procedure of Example 1 and in place of N-methylbenzamide and starting with 4-chloro-N-methylbenzamide, and in place of trimethylacetylchloride, and starting with,
b. 2,2-dimethyl-4-pentoyl chloride, or
c. methacryloylchloride,
the following products are obtained,
b. 3-(1,1-dimethyl-3-butenyl)-5-chloro-3-hydroxy-2-methylphthalimidine m.p. 138°–140°C.,
c. 3-hydroxy-3-isopropenyl-5-chloro-2-methylphthalimidine m.p. 175°–177°C., respectively.

EXAMPLE 5

Following the procedure of Example 1 and in place of trimethylacetylchloride and starting with,
a. 2-methylbutanoyl chloride,
b. 2,2-tetramethylenepropanoyl chloride, or
c. 2,2,3-trimethyl-3-butanoyl chloride,
the following products are obtained,
a. 3-(1-ethyl-2-methylpropyl)-3-hydroxy-2-methylphthalimidine,
b. 3-hydroxy-2-methyl-3-(1-methylcyclopentyl)phthalimidine, or
c. 3-hydroxy-2-methyl-3-(1,1,2-trimethylallyl)phthalimidine, respectively.

EXAMPLE 6

3-t-butyl-5-chloro-3-hydroxy-2-methylphthalimidine

To a flask equipped with a stirrer, dropping funnel, condenser and gas inlet tube maintained under a nitrogen atmosphere there was added at room temperature 15.2 g (0.087 mole) of 4-chloro-N-methylbenzamide in 150 ml. dry tetrahydrofuran. The reaction flask was immersed in dry ice-isopropanol bath and cooled to an internal temperature of −60°C. Stirring was initiated and 152 ml. of 1.6 M of n-butyllithium (0.240 mole) in hexane was added dropwise in ca. 1 hour maintaining the temperature below −60°C. The resulting red dilithio salt (compound VII) was stirred at −60°C. for 1 hour longer. To the cold solution, a solution of 12.9 g. (0.087 mole) of trimethylacetylchloride (pivaloyl chloride) in 75 ml. anhydrous tetrahydrofuran was added dropwise in ca. 45 minutes maintaining the temperature between −60° and −40°C. The resulting solution was stirred 2 hours at −50°C. and allowed to warm to 0°C. and the resulting adduct treated with 100 ml. saturated aqueous ammonium chloride maintaining the temperature below 10°C. The layers were separated and the tetrahydrofuran dried over anhydrous magnesium sulfate, filtered and evaporated in vacuo. The resulting oil was triturated with cold ether and filtered to give 3-t-butyl-5-chloro-3-hydroxy-2-methylphthalimidine m.p. 192°C.

EXAMPLE 7

3-t-butyl-5-chloro-3-hydroxy-2-ethylphthalimidine

Step A 3-t-butyl-5-chloro-3-hydroxy-2-phenylphthalimidine

To a flask equipped with a stirrer, dropping funnel, condenser and gas inlet tube maintained under a nitrogen atmosphere there was added 50g (0.216 mole) of 4-chlorobenzanilide and 1.0 liter tetrahydrofuran. The mixture was cooled to −60°C and 318ml (0.475 mole)

of n-butyllithium (15% in hexane) was added dropwise keeping temperature between −50° and −60°C. After the addition was complete the mixture was stirred at −60°C for 2 hours and then 25.99 (0.216 mole) of pivaloyl chloride in 200ml tetrahydrofuran was added dropwise maintaining the temperature between −50°C to −60°C. The mixture was stirred 2 hours at −60°C., warmed to −20°C. and treated with 200ml of saturated ammonium chloride solution. The mixture was filtered, the layers separated and the organic layer dried over anhyd. magnesium sulfate, filtered and evaporated. The resulting white solid was triturated with ether to give 3-butyl-5-chloro-3-hydroxy-2-phenylphthalimidine, m.p. 198.5° − 200.5°C.

Step B 3-t-butyl-5-chloro-3-hydroxyphthalide

A mixture of 42g (0.136 mole) of 3-t-butyl-5-chloro-3-hydroxy-2-phenylphthalimidine, 50g (0.720 mole) of potassium hydroxide, 300ml of ethylene glycol and 150ml water was refluxed for 24 hours. The solvents were removed in vacuo and water added to the residue and filtered. The filtrate was acidified with conc. hydrochloric acid and the white slurry filtered and recrystallized from isopropanol-water (1:1) to give 3-t-butyl-5-chloro-3-hydroxyphthalide, m.p. 160° − 161°C.

Step C 3-t-butyl-5-chloro-3-hydroxy-2-ethylphthalimidine

A mixture of 4.09 (0.016 mole) of 3-t-butyl-5-chloro-3-hydroxyphthalide, 3ml (0.04 mole) of thionyl chloride and 100ml of benzene was refluxed for 2 hours. The solvent was removed in vacuo and the residue dissolved in 50ml of ether and added to 25g of a 70% solution of ethylamine in water (0.26 mole). The resulting mixture was stirred 18 hours at room temperature and the solvents were removed in vacuo. The resulting yellow solid was purified by trituration with water to give 3-t-butyl-5-chloro-3-hydroxy-2-ethylphthalimidine, m.p. 144° − 145°C.

EXAMPLE 8

Following the procedure of Example 7, step B and in place of 3-t-butyl-5-chloro-3-hydroxy-2-phenylphthalimidine and starting with the correspondingly lettered product of Example 2, the following compounds of formula (II) are prepared,
a. 3-t-butyl-3-hydroxy-5-methoxyphthalide,
b. 3-t-butyl-5-chloro-3-hydroxyphthalide,
c. 3-t-butyl-7-chloro-3-hydroxyphthalide,
d. 3-t-butyl-3-hydroxyphthalide,
e. 3-t-butyl-5-fluoro-3-hydroxyphthalide,
f. 3-t-butyl-3-hydroxy-5-phenylphthalide,
g. 3-t-butyl-5-dimethylamino-3-hydroxyphthalide,
h. 3-t-butyl-3-hydroxy-6-methoxyphthalide,
i. 3-t-butyl-2,5-dimethyl-3-hydroxyphthalide,
j. 3-t-butyl-5,6-dichloro-3-hydroxyphthalide,
k. 3,5-bis(t-butyl)-3-hydroxyphthalide,
l. 3-t-butyl-5-ethyl-3-hydroxyphthalide,
m. 3-t-butyl-5-chloro-3-hydroxyphthalide,
n. 3-t-butyl-4,5-dimethoxy-3-hydroxyphthalide,
o. 3-t-butyl-3-hydroxy-5 or 6-nitrophthalide,
p. 5 or 6-amino-3-t-butyl-3-hydroxyphthalide, or
q. 3-t-butyl-3-hydroxy-5,6-methylenedioxyphthalide, respectively.

EXAMPLE 9

Following the procedure of Example 7, step B and in place of 3-t-butyl-5-chloro-3-hydroxy-2-phenylphthalimidine, and starting with the correspondingly lettered product of Example 3, the following compounds of formula (II) are obtained,
a. 3-t-butyl-3-hydroxy-7-methoxyphthalide,
b. 3-t-butyl-3-hydroxy-4,7-bis(trisfluoromethyl)phthalide,
c. 3-t-butyl-3-hydroxy-4-methylphthalide, or
d. 3-t-butyl-3-hydroxy-4-methoxyphthalide, respectively.

EXAMPLE 10

Following the procedure of Example 7, step B and in place of 3-t-butyl-5-chloro-3-hydroxy-2-phenylphthalimidine, and starting with the correspondingly lettered product of Example 4, the following compounds of formula (II) are obtained,
a. 3-(1-[1,1-cyclopentamethylene]ethyl)-3-hydroxyphthalide,
b. 3-(1,1-dimethyl-3-butenyl)-5-chloro-3-hydroxyphthalide,
c. 3-hydroxy-3-isopropenyl-5-chlorophthalide, or
d. 3-(1-[1,1-cyclohexamethylene]ethyl)-3-hydroxyphthalide, respectively.

EXAMPLE 11

Following the procedure of Example 7, step B and in place of 3-t-butyl-5-chloro-3-hydroxy-2-phenylphthalimidine, and starting with the correspondingly lettered product of Example 5, the following compounds of formula (II) are obtained,
a. 3-(1-ethyl-2-methylpropyl)-3-hydroxyphthalide,
b. 3-hydroxy-3-(1-methylcyclopentyl)phthalide, or
c. 3-hydroxy-3-(1,1,2-trimethylallyl)phthalide, respectively.

EXAMPLE 12

3-amino-3-t-butyl-2-methylphthalimidine

A solution of 8g (0.0036 mole) of 3-t-butyl-3-hydroxy-2-methylphthalimidine, 40ml thionyl chloride and 75ml benzene was refluxed for 2 hours. The solvents were removed in vacuo and the resulting oil dissolved in 15ml of benzene and added to a solution of benzene saturated with ammonia and the mixture stirred at room temperature for 18 hours. The solvents were removed in vacuo and the residue dissolved in methylene chloride, washed with 100ml 2N sodium hydroxide, dried over anhyd. magnesium sulfate and evaporated in vacuo. The resulting solid was filtered, washed with water and dried to give 3-amino-3-t-butyl-2-methylphthalimidine, m.p. 195° − 195.5°C.

EXAMPLE 13

Following the procedure of Example 12 and in place of 3-t-butyl-3-hydroxy-2-methylphthalimidine, and starting with the correspondingly lettered product of Example 2, the following compounds of formula (Ib) are prepared.
a. 3-amino-3-t-butyl-5-methoxy-2-methylphthalimidine,
b. 3-amino-3-t-butyl-5-chloro-2-methylphthalimidine,
c. 3-amino-3-t-butyl-7-chloro-2-methylphthalimidine,
d. 3-amino-3-t-butyl-2-phenylphthalimidine,
e. 3-amino-3-t-butyl-5-fluoro-2-methylphthalimidine, f. 3-amino-3-t-butyl-2-methyl-5-phenylphthalimidine-2-methyl,
g. 3-amino-3-t-butyl-5-dimethylamino-2-methylphthalimidine,
h. 3-amino-3-t-butyl-6-methoxy-2-methylphthalimidine,
i. 3-amino-3-t-butyl-2,5-dimethyl-2-methylphthalimidine,
j. 3-amino-3-t-butyl-5,6-dichloro-2-methylphthalimidine,
k. 3-amino-3,5-bis(t-butyl)-2-methylphthalimidine,
l. 3-amino-3-t-butyl-5-ethyl-2-methylphthalimidine,
m. 3-amino-3-t-butyl-5-chloro-2-ethylphthalimidine,
n. 3-amino-3-t-butyl-4,5-dimethoxy-2-methylphthalimidine,
o. 3-amino-3-t-butyl-2-methyl-5 or 6-nitrophthalimidine,
p. 3,5 or 6-amino-3-t-butyl-2-methylphthalimidine, or
q. 3-amino-3-t-butyl-2-methyl-5,6-methylenedioxyphthalimidine, respectively.

EXAMPLE 14

Following the procedure of Example 12 and in place of 3-t-butyl-3-hydroxy-2-methylphthalimidine, and starting with the correspondingly lettered product of Example 3, the following compounds of formula (Ib) are prepared,
a. 3-amino-3-t-butyl-7-methoxy-2-methylphthalimidine,
b. 3-amino-3-t-butyl-2-methyl-4,7-bis(trifluoromethyl)phthalimidine,
c. 3-amino-3-t-butyl-2,4-dimethylphthalimidine, or
d. 3-amino-3-t-butyl-4-methoxy-2-methylphthalimidine, respectively.

EXAMPLE 15

Following the procedure of Example 12 and in place of 3-t-butyl-3-hydroxy-2-methylphthalimidine, and starting with the correspondingly lettered product of Example 4 the following compounds of formula (Ib) are prepared,
a. 3-amino-3-(1-[1,1-cyclopentamethylene]ethyl)-2-methylphthalimidine,
b. 3-amino-3-(1,1-dimethyl-3-butenyl)-5-chloro-2-methylphthalimidine
c. 3-amino-3-isopropenyl-5-chloro-2-methylphthalimidine, or
d. 3-amino-3-(1-[1,1-cyclohexamethylene]ethyl)-3-hydroxy-2-methylphthalimidine, respectively.

EXAMPLE 16

Following the procedure of Example 12 and in place of 3-t-butyl-3-hydroxy-2-methylphthalimidine, and starting with the correspondingly lettered product of Example 5, the following compounds of formula (Ib) are prepared,
a. 3-amino-3-(1-ethyl-2-methylpropyl)-2-methylphthalimidine,
b. 3-amino-2-methyl-3-(1-methylcyclopentyl)phthalimidine, or
c. 3-amino-2-methyl-3-(1,1,2-trimethylallyl)phthalimidine, respectively.

EXAMPLE 17

3-t-butyl-3-methoxy-2-methylphthalimidine

A solution of 8g (0.0036 mole) of 3-t-butyl-3-hydroxy-2-methylphthalimidine, 40ml of thionyl chloride and 75ml of benzene was refluxed for 2 hrs. The solvent was removed in vacuo and the resulting oil was dissolved in 100ml methanol and allowed to stand at room temperature for 18 hours. The solvent was removed in vacuo to give 3-t-butyl-3-methoxy-2-methylphthalimidine as an oil, identified by CHN analysis, NMR & IR.

EXAMPLE 18

Following the procedure of Example 17 and in place of 3-t-butyl-3-hydroxy-2-methylphthalimidine, and starting with the correspondingly lettered product of Example 2, the following compounds of formula (Ic) are prepared,
a. 3-t-butyl-3,5-dimethoxy-2-methylphthalimidine,
b. 3-t-butyl-5-chloro-3-methoxy-2-methylphthalimidine,
c. 3-t-butyl-7-chloro-3-methoxy-2-methylphthalimidine,
d. 3-t-butyl-3-methoxy-2-phenylphthalimidine,
e. 3-t-butyl-5-fluoro-3-methoxy-2-methylphthalimidine,
f. 3-t-butyl-3-methoxy-2-methyl-5-phenylphthalimidine,
g. 3-t-butyl-5-dimethylamino-3-methoxy-2-methylphthalimidine,
h. 3-t-butyl-3,6-dimethoxy-2-methylphthalimidine,
i. 3-t-butyl-2,5-dimethyl-3-methoxy-2-methylphthalimidine,
j. 3-t-butyl-5,6-dichloro-3-methoxy-2-methylphthalimidine,
k. 3,5-bis(t-butyl)-3-methoxy-2-methylphthalimidine,
l. 3-t-butyl-5-ethyl-3-methoxy-2-methylphthalimidine,
m. 3-t-butyl-5-chloro-2-ethyl-3-methoxy-5-methylphthalimidine,
n. 3-t-butyl-3,4,5-trimethoxy-2-methylphthalimidine,
o. 3-t-butyl-3-methoxy-2-methyl-5 or 6-nitrophthalimidine,
p. 5 or 6-amino-3-t-butyl-3-methoxy-2-methylphthalimidine, or
q. 3-t-butyl-3-methoxy-2-methyl-5,6-methylenedioxyphthalimidine, respectively.

EXAMPLE 19

Following the procedure of Example 17 and in place of 3-t-butyl-3-hydroxy-2-methylphthalimidine, and starting with the correspondingly lettered product of Example 3, the following compounds of formula (Ic) are prepared,
a. 3-t-butyl-3,7-dimethoxy-2-methylphthalimidine,
b. 3-t-butyl-3-methoxy-2-methyl-4,7-bis(trifluoromethyl)phthalimidine,
c. 3-t-butyl-2,4-dimethyl-3-methoxyphthalimidine, or
d. 3-t-butyl-3,4-dimethoxy-2-methylphthalimidine, respectively.

EXAMPLE 20

Following the procedure of Example 17 and in place of 3-t-butyl-3-hydroxy-2-methylphthalimidine, and starting with the correspondingly lettered product of Example 4, the following compounds of formula (Ic) are prepared,
a. 3-(1-[1,1-cyclopentamethylene]ethyl)-3-methoxy-2-methylphthalimidine,
b. 3-(1,1-dimethyl-3-butenyl)-5-chloro-3-methoxy-2-methylphthalimidine,
c. 3-isopropenyl-5-chloro-3-methoxy-2-methylphthalimidine, or d. 3-(1-[1,1-cyclohexamethylene]ethyl-3-methoxy-2-methylphthalimidine, respectively.

EXAMPLE 21

Following the procedure of Example 17 and in place of 3-t-butyl-3-hydroxy-2-methylphthalimidine, and starting with the correspondingly lettered product of Example 5, the following compounds of formula (Ic) are prepared,
a. 3-(1-ethyl-2-methylpropyl)-3-methoxy-2-methylphthalimidine,
b. 3-methoxy-2-methyl-3-(1-methylcyclopentyl)phthalimidine, or
c. 3-methoxy-2-methyl-3-(1,1,2-trimethylallyl)phthalimidine, respectively.

EXAMPLE 22

3-t-butyl-3-(2-[dimethylamino]ethylamino)-2-methylphthalimidine

A solution of 8g (0.0036 mole) of 3-t-butyl-3-hydroxy-2-methylphthalimidine, 40ml thionyl chloride and 75ml benzene was refluxed for 2 hours. The solvents were removed in vacuo and the resulting oil dissolved in 15ml benzene and added to a solution of 11.5ml (0.102 mole) of unsymmetrical dimethylethylenediamine in 50ml benzene and the mixture stirred at room temperature for 18 hours. The solvents were removed in vacuo and the residue dissolved in methylenechloride, washed with 100 ml 2N sodium hydroxide, dried over anhyd. magnesium sulfate and evaporated in vacuo. The resulting oil was dissolved in isopropanol, treated with gaseous hydrogen chloride and the solid recrystallized from acetonitrile to give 3-t-butyl-3-(2-[dimethylamino]ethylamino)-2-methylphthalimidine dihydrochloride, m.p. 142° – 143.5°C.

EXAMPLE 23

Following the procedure of Example 22 and in place of 3-t-butyl-3-hydroxy-2-methylphthalimidine and starting with the correspondingly lettered product of Example 2, the following compounds of formula (Id) are prepared as the dihydrochloride
a. 3-t-butyl-3(2-[dimethylamino]ethylamino)-5-methoxy-2-methylphthalimidine,
b. 3-t-butyl-5-chloro-3-(2-[dimethylamino]ethylamino)-2-methylphthalimidine,
c. 3-t-butyl-7-chloro-3-(2-[dimethylamino]ethylamino)-2-methylphthalimidine,
d. 3-t-butyl-3-(2-[dimethylamino]ethylamino)-2-phenylphthalimidine,
e. 3-t-butyl-3-(2-[dimethylamino]ethylamino)-2-methylphthalimidine,
f. 3-t-butyl-3-(2-[dimethylamino]ethylamino)-2-methyl-5-phenyl phthalimidine,
g. 3-t-butyl-5-dimethylamino-3-(2-[dimethylamino]ethylamino)-2-methylphthalimidine,
h. 3-t-butyl-3-(2-[dimethylamino]ethylamino)-6-methoxy-2-methylphthalimidine,
i. 3-t-butyl-3,5-dimethyl-3-(2-[dimethylamino]ethylamino)-2-methylphthalimidine,
j. 3-t-butyl-5,6-dichloro-3-(2-[dimethylamino]ethylamino)-2-methylphthalimidine,
k. 3,5-bis(t-butyl)-3-(2-[dimethylamino]ethylamino)-2-methylphthalimidine,
l. 3-t-butyl-3-(2-[dimethylamino]ethylamino)-3-ethyl-2-methylphthalimidine,
m. 3-t-butyl-5-chloro-2-ethyl-3-(2-[dimethylamino]ethylamino)phthalimidine,
n. 3-t-butyl-2,5-dimethoxy-3-(2-[dimethylamino]ethylamino)-2-methylphthalimidine,
o. 3-t-butyl-3-(2-[dimethylamino]ethylamino)-2-methyl-5 or 6-nitrophthalimidine,
p. 5 or 6-amino-3-t-butyl-3-(2-[dimethylamino]ethylamino)-2-methylphthalimidine, or
q. 3-t-butyl-3-(2-[dimethylamino]ethylamino)-2-methyl-5,6-methylenedioxyphthalimidine, respectively

EXAMPLE 24

Following the procedure of Example 22 and in place of 3-t-butyl-3-hydroxy-2-methylphthalimidine and starting with the correspondingly lettered product of Example 3, the following compounds of formula (Id) are prepared,
a. 3-t-butyl-3-(2-[dimethylamino]ethylamino)-7-methoxy-2-methylphthalimidine,
b. 3-t-butyl-3-(2-[dimethylamino]ethylamino)-2-methyl-4,7-bis(trifluoromethyl)phthalimidine,
c. 3-t-butyl-2,4-dimethyl-3-(2-[dimethylamino]ethylamino)phthalimidine, or
d. 3-t-butyl-3-(2-[dimethylamino]ethylamino)-4-methoxy-2-methylphthalimidine, respectively.

EXAMPLE 25

Following the procedure of Example 22 and in place of 3-t-butyl-3-hydroxy-2-methylphthalimidine, and starting with the appropriately lettered product of Example 4, the following compounds of formula (Id) are prepared,
a. 3-(1-[1,1-cyclopentamethylene]ethyl)-3-(2-[dimethylamino]ethylamino)-2-methylphthalimidine,
b. 3-(1,1-dimethyl-3-butenyl)-5-chloro-3-(2-[dimethylamino]ethylamino)-2-methylphthalimidine,
c. 3-(2-[dimethylamino]ethylamino-5-chloro-3-isopropenyl-2-methylphthalimidine, or
d. 3-(1-[1,1-cyclohexamethylene]ethyl)-3-(2-[dimethylamino]ethyl)-2-methylphthalimidine, respectively.

EXAMPLE 26

Following the procedure of Example 22 and in place of 3-t-butyl-3-hydroxy-2-methylphthalimidine, and starting with the correspondingly lettered product of Example 5, the following compounds of formula (Id) are prepared,
a. 3-(1-ethyl-2-methylpropyl)-3-(2-[dimethylamino]ethylamino)-2-methylphthalimidine,
b. 3-(2-[dimethylamino]ethylamino)-2-methyl-3-(1-methylcyclopentyl) phthalimidine, or
c. 3-(2-[dimethylamino]ethylamino)-2-methyl-3-(1,1,2-trimethylallyl) phthalimidine, respectively.

EXAMPLE 27

3-t-butyl-5,6-dichloro-3-hydroxy-2-methylphthalimidine

To a suspension of 1.8g (0.065 g-atoms) of magnesium turnings in 50ml dry tetrahydrofuran under nitrogen was added dropwise 6.3g (0.065 mole) of 2-chloro-2-methyl propane in 100ml dry tetrahydrofuran and the reaction catalyzed with a drop of ethyl bromide. After the addition was complete the mixture was refluxed for 2 hours cooled to room temperature and then 10g (0.0435 mole) of 4,5-dichloro-2-methylphthalimide in 200ml tetrahydrofuran was added dropwise and the resulting mixture refluxed for 18 hours. The mixture was cooled in ice and treated with 100ml water, filtered and the layers separated. The organic layers was dried over anhyd. magnesium sulfate, filtered and evaporated and the residue recrystallized from isopropanol-water (1:1) to give 3-t-butyl-5,6-dichloro-3-hydroxy-2-methylphthalimidine hydrate, m.p. 195.5° – 196.5°C.

EXAMPLE 28

3-t-butyl-3-hydroxy-2-methyl-5 or 6-nitrophthalimidine

A solution of 20g (0.09 mole) 3-t-butyl-3-hydroxy-2-methylphthalimidine in 80ml conc. sulfuric acid was cooled to 0°C. and a solution of 13.0g (0.129 mole) of potassium nitrate in 80ml conc. sulfuric acid was added dropwise with stirring keeping the temperature at 0°C. Stirring was continued at 0°C. for 1 hour after addition and then at room temperature for 24 hours. The solution was poured on to 1200g ice and extracted twice with 250ml chloroform. The chloroform extract was washed four times with 125ml, 10% sodium bicarbonate and twice with 150ml water, dried over anhyd. magnesium sulfate, filtered and evaporated. The resulting solid was recrystallized from isopropanol-water (1:1) to give 3-t-butyl-3-hydroxy-2-methyl-5 or 6-nitrophthalimidine, m.p. 210° – 212°C.

EXAMPLE 29

3-amino-3-t-butyl-2-methylphthalimidine

To a flask equipped with a stirrer, dropping funnel, condenser and gas inlet tube maintained under a nitrogen atmosphere there was added at room temperature 15.2g.(0.108 mole) of N-methylbenzamide in 150 ml. dry tetrahydrofuran. The reaction flask was immersed in an ice bath and cooled to an internal temperature of 5°C. Stirring was initiated and 152 ml. of 1.6 M of n-butyllithium (0.240 mole) in hexane was added dropwise in ca. 1 hour maintaining the temperature below 8°C. The resulting red dilithio salt (Compound VII) was stirred at 5°C for 1 hour longer and then 8.95g (0.108 mole) of trimethylacetonitrile (pivaloyl nitrile) in 75ml tetrahydrofuran was added dropwise to the cold solution. At the completion of the addition, the mixture was refluxed for 4½ hours, cooled in ice and treated with 100ml saturated ammonium chloride solution maintaining the temperature below 10°C. The resulting solid was filtered, washed with water and dried to give 3-amino-3-t-butyl-2-methylphthalimidine, m.p. 195° – 195.5°C.

EXAMPLE 30

Following the procedure of Example 7, step c and in place of 3-t-butyl-5-chloro-3-hydroxyphthalide starting with 3-t-butyl-3-hydroxy-2-phenylphthalide, and in place of ethylamine and starting with,
a. allylamine,
b. benzylamine,
c. N-methylcarbamoyloxyamine,
d. carbethoxymethylamine, or
e. ethanolamine,
the following products of formula (Ia) are obtained
a. 2-allyl-3-t-butyl-3-hydroxyphthalimidine, m.p. 126°–127°C.,
b. 2-benzyl-3-t-butyl-3-hydroxyphthalimidine, m.p. 172°–173°C.,
c. 3-t-butyl-3-hydroxy-2-N-methylcarbamoyloxyphthalimidine, m.p. 98°C dec.,
d. 3-t-butyl-2-carbethoxymethyl-3-hydroxyphthalimidine, m.p. 140°–141°C., or
e. 3-t-butyl-3-hydroxy-2-(2-hydroxyethyl)phtalimidine, m.p. 121°–124°C., respectively.

EXAMPLE 31

Following the procedure of Example 12 and in place of 3-t-butyl-3-hydroxy-2-methylphthalimidine, and starting with the correspondingly lettered product of Example 30, the following compounds of formula (Ib) are prepared,
a. 2-allyl-3-amino-3-t-butylphthalimidine,
b. 3-amino-2-benzyl-3-t-butylphthalimidine,
c. 3-amino-3-t-butyl-2-N-methylcarbamoyloxyphthalimidine,
d. 3-amino-3-t-butyl-2-carbethoxymethylphthalimidine, or
e. 3-amino-3-t-butyl-2-(2-hydroxyethyl)phthalimidine, respectively.

EXAMPLE 32

Following the procedure of Example 17 and in place of 3-t-butyl-3-hydroxy-2-methylphthalimidine, and starting with the correspondingly lettered product of Example 30, the following compounds of formula (Ic) are prepared,
a. 2-allyl-3-t-butyl-3-methoxyphthalimidine,
b. 2-benzyl-3-t-butyl-3-methoxyphthalimidine,
c. 3-t-butyl-3-methoxy-2-N-methylcarbamoyloxyphthalimidine
d. 3-t-butyl-2-carbethoxymethyl-3-methoxyphthalimidine, or
e. 3-t-butyl-2-(2-hydroxyethyl)-3-methoxyphthalimidine, respectively.

EXAMPLE 33

Following the procedure of Example 22 and in place of 3-t-butyl-3-hydroxy-2-methylphthalimidine, and starting with the correspondingly lettered product of Example 30, the following compounds of formula (Id) are prepared,
a. 2-allyl-3-t-butyl-3-(2-[dimethylamino]ethylamino)phthalimidine,
b. 2-benzyl-3-t-butyl-3-(2-[dimethylamino]ethylamino)phthalimidine,
c. 3-t-butyl-3-(2-[dimethylamino]ethylamino)-2-N-methylcarbamoyloxyphthalimidine,
d. 3-t-butyl-2-carbethoxymethyl-3-(2-[dimethylamino]ethylamino)phthalimidine, or
e. 3-t-butyl-3-(2-[dimethylamino]ethylamino)-2-(2-hydroxyethyl)phthalimidine, respectively.

EXAMPLE 34

Following the procedure of Example 27 and in place of 4,5-dichloro-2-methylphthalimidine and starting with,
a. 2-phenylphthalimide,
b. 4,7-dimethoxy-2-methylphthalimide,
c. 4,7-bis(trifluoromethyl)-2-methylphthalimide,
d. 2,5,6-trimethylphthalimide,
e. 5,6-dimethoxy-2-methylphthalimide,
the following products are obtained,
a. 3-t-butyl-3-hydroxy-2-phenylphthalimidine,
b. 3-t-butyl-4,7-dimethoxy-3-hydroxy-2-methylphthalimidine, c. 3-t-butyl-3-hydroxy-2-methyl-4,7-bis(trifluoromethyl)phthalimidine,
d. 3-t-butyl-3-hydroxy-2,5,6-trimethylphthalimidine,
e. 3-t-butyl-5,6-dimethoxy-3-hydroxy-2-methylphthalimidine, respectively.

EXAMPLE 35

Following the procedure of Example 29 and in place of N-methylbenzamide and starting with the correspondingly lettered starting materials of Example 2, the correspondingly lettered compounds of formula (Ib) of Example 13 are obtained.

EXAMPLE 36

Following the procedure of Example 29 and in place of N-methylbenzamide and starting with the correspondingly lettered starting materials of Example 3, the correspondingly lettered compounds of formula (Ib) of Example 14 are obtained.

EXAMPLE 37

Following the procedure of Example 29 and in place of trimethylacetonitrile, and starting with,
a. 2,2-pentamethylenepropionitrile, or
d. 2,2-hexamethylenepropionitrile,
the following products are obtained,
a. 3-amino-3-(1-[1,1-cyclopentamethylene]ethyl)-2-methylphthalimidine, or
d. 3-amino-3-(1-[1,1-cyclohexamethylene]ethyl-3-hydroxy-2-methylphthalimidine, respectively.

Following the procedure of Example 29 and in place of N-methylbenzamide and starting with 4-chloro-N-methylbenzamide, and in place of trimethylacetonitrile, and starting with,
b. 2,2-dimethyl-4-pentenonitrile, or
c. methacrylonitrile,
the following products are obtained,
b. 3-amino-3-(1,1-dimethyl-3-butenyl)-5-chloro-2-methylphthalimidine, or
c. 3-amino-3-isopropenyl-5-chloro-2-methylphthalimidine, respectively.

EXAMPLE 38

Following the procedure of Example 29, and in place of trimethylacetonitrile, and starting with,
a. 2-methylbutanonitrile,
b. 2,2-tetramethylenepropanionitrile, or
c. 2,2,3-trimethyl-3-butanonitrile,
The correspondingly lettered compounds of formula (Ib) of Example 16 are obtained.

EXAMPLE 39

Following the procedure of Example 7, step C, and in place of ethylamine and starting with
a. propylamine or
b. allylamine,
the following products of formula (Ia) are obtained
a. 3-t-butyl-5-chloro-3-hydroxy-2-propylphthalimidine, m.p. 129°–131°C, or
b. 2-allyl-3-t-butyl-5-chloro-3-hydroxyphthalimidine, m.p. 125°–126.5°C, respectively.

EXAMPLE 40

Following the procedure of Example 7, step C and in place of 3-t-butyl-5-chloro-3-hydroxyphthalide and starting with
a. 3-t-butyl-3-hydroxy-5-methoxyphthalide, or
b. 3-t-butyl-3-hydroxy-5-methylphthalide
the following products of formula (Ia) are obtained
a. 3-t-butyl-2-ethyl-3-hydroxy-5-methoxyphthalimidine m.p. 180°–182°C or
b. 3-t-butyl-2-ethyl-3-hydroxy-5-methylphthalimidine m.p. 143°–144°C, respectfully.

EXAMPLE 41

Following the procedure of Example 7, step C and in place of 3-t-butyl-5-chloro-3-hydroxyphthalide starting with 3-t-butyl-3-hydroxyphthalide, and in place of ethylamine and starting with
a. propylamine
b. isopropylamine
the following products are obtained
a. 3-t-butyl-3-hydroxy-2-propylphthalimidine m.p. 134°–135.5°C, or
b. 3-t-butyl-3-hydroxy-2-isopropylphthalimidine, m.p. 160°–161.5°C respectfully.

EXAMPLES 42 and 43

Tablets and Capsules Suitable for Oral Administration

Tablets and capsules containing the ingredients indicated below may be prepared by conventional techniques and are useful as minor tranquilizers-sedative hypnotics at a dose of one tablet or capsule 2 to 4 times a day.

| Ingredients | Weight (mg) tablet | capsule |
|---|---|---|
| 3-t-butyl-5-chloro-3-hydroxy-2-methyl-phthalimidine | 25 | 25 |
| tragacanth | 10 | — |
| lactose | 222.5 | 275 |
| corn starch | 25 | |
| talcum | 15 | |
| magnesium stearate | 2.5 | |

EXAMPLES 44 and 45

Sterile Suspension for Injection and Oral Liquid Suspension

The following pharmaceutical compositions are formulated with the indicated amount of active agent using conventional techniques. The injectable suspension and the oral liquid suspension represent formulations useful as unit doses and may be administered as minor tranquilizers-sedative hypnotics. The injectable suspension is suitable for administration once a day whereas the oral liquid suspension is suitably administered 2 to 4 times per day for this purpose.

| Ingredients | Weight (mg) Sterile Injectable Suspension | Oral Liquid Suspension |
|---|---|---|
| 3-t-butyl-5-chloro-3-hydroxy-2-methyl-phthalimidine | 25 | 25 |
| sodium carboxy methyl cellulose U.S.P. | 1.25 | 12.5 |
| methyl cellulose | 0.4 | — |

| Ingredients | Weight (mg) Sterile Injectable Suspension | Oral Liquid Suspension |
|---|---|---|
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g., Tween 80), U.S.P. | — | 5 |
| sorbitol solution, 70%, U.S.P. | — | 2,500 |
| buffer agent to adjust pH for desired stability | q.s. | q.s. |
| water | for injection, q.s. to 1 ml. | q.s. to 5 ml. |

EXAMPLES 46 and 47

Following the procedures of Examples 42 and 43, and in place of 3-t-butyl-5-chloro-3-hydroxy-2-methylphthalimidine starting with,
a. 3-t-butyl-3-hydroxy-2-methylphthalimidine,
b. 3-t-butyl-3-hydroxy-5-methoxy-2-methylphthalimidine,
c. 3-t-butyl-2,5-dimethyl-3-hydroxy-2-methylphthalimidine, or
d. 3-t-butyl-2-ethyl-3-hydroxy-5-methylphthalimidine, tablets and capsules may be prepared which are useful as minor tranquilizers-sedative hypnotics at a dose of one tablet or capsule 2 to 4 times a day.

EXAMPLES 48 and 49

Following the procedures of Examples 44 and 45, and in place of 3-t-butyl-5-chloro-3-hydroxy-2-methylphthalimidine starting with,
a. 3-t-butyl-3-hydroxy-2-methylphthalimidine,
b. 3-t-butyl-3-hydroxy-5-methoxy-2-methylphthalimidine,
c. 3-t-butyl-2,5-dimethyl-3-hydroxy-2-methylphthalimidine, or
d. 3-t-butyl-2-ethyl-3-hydroxy-5-methylphthalimidine, injectable suspensions and oral liquid suspensions may be prepared which are useful as minor tranquilizers-sedative hypnotics at a dose of one tablet or capsule 2 to 4 times a day.

What is claimed is:
1. A compound of the formula:

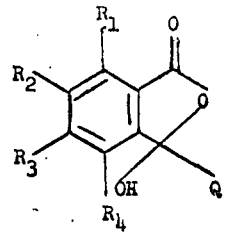

where $R_1$ is hydrogen, lower alkoxy, halo having an atomic weight of 19 to 36, or trifluoromethyl, $R_2$ is hydrogen, lower alkyl, lower alkoxy, halo having an atomic weight of 19 to 36, trifluoromethyl, nitro or amino, $R_3$ is hydrogen, lower alkyl, lower alkoxy, halo having an atomic weight of 19 to 36, trifluoromethyl, nitro, amino, dialkylamino or phenyl, $R_4$ is hydrogen, lower alkyl, lower alkoxy, or trifluoromethyl, $R_6$ and $R_7$ together are $-(CH_2)_n-$ where $n$ is 4, 5, or 6, $R_8$ is methyl, vinyl or allyl, or

where $R_9$ is lower alkyl,
provided that
1. no more than two of $R_1$, $R_2$, $R_3$ or $R_4$ are other than hydrogen,
2. when either of $R_1$ or $R_3$ is halo, the other of $R_1$ or $R_3$ is not halo,
3. only one of $R_1$ and $R_3$, or $R_2$ and $R_4$ is alkoxy at one time,
4. there are no two trifluoromethyl groups on adjacent carbon atoms,
5. only one of $R_2$ or $R_3$ is nitro or amino.

* * * * *